United States Patent [19]

Neuhäuser

[11] 4,273,117
[45] Jun. 16, 1981

[54] APPARATUS FOR DRILLING BONE

[76] Inventor: Hans G. Neuhäuser, Moorhaldenstrasse 22,, 7130 Mühlacker, Fed. Rep. of Germany

[21] Appl. No.: 69,625

[22] Filed: Aug. 24, 1979

[30] Foreign Application Priority Data

Sep. 2, 1978 [DE] Fed. Rep. of Germany ....... 2838348

[51] Int. Cl.³ .................. A61F 5/04; A61F 17/32; A61B 17/16; B23B 51/00
[52] U.S. Cl. .................. 128/92 E; 128/305; 128/310; 408/209; 408/212
[58] Field of Search ............. 128/92 E, 92 EB, 305, 128/305.1, 310; 408/59, 211, 212, 207, 209

[56] References Cited

U.S. PATENT DOCUMENTS

| 930,477 | 8/1909 | Hudson | 128/310 |
|---|---|---|---|
| 2,487,221 | 11/1949 | Cooke | 408/211 |
| 2,842,131 | 7/1958 | Smith | 128/310 |
| 3,028,772 | 4/1962 | Mossberg | 408/59 |
| 3,028,773 | 4/1962 | Borneman | 408/211 |
| 3,702,611 | 11/1972 | Fishbein | 128/305 |
| 3,719,186 | 3/1973 | Merig, Jr. | 128/92 EB |
| 3,815,605 | 6/1974 | Schmidt et al. | 128/92 E |
| 4,004,581 | 1/1977 | Heimke et al. | 128/305 |

FOREIGN PATENT DOCUMENTS

| 2284308 | 4/1976 | France | 128/305 |
|---|---|---|---|
| 434703 | 9/1935 | United Kingdom | 408/59 |
| 978131 | 12/1964 | United Kingdom | 408/59 |
| 1001133 | 8/1965 | United Kingdom | 408/59 |
| 1070102 | 5/1967 | United Kingdom | 408/59 |
| 1466961 | 3/1977 | United Kingdom | 408/59 |

Primary Examiner—Kyle L. Howell
Assistant Examiner—C. W. Shedd
Attorney, Agent, or Firm—Shenier & O'Connor

[57] ABSTRACT

An apparatus for forming a hole in a bone is provided, which comprises a body, a drill bit rotatable with respect to the body, and, in order to locate the drill, a mandrel coaxial with the drill bit, slidably projectable through the drill bit and biased to an extended position.

20 Claims, 6 Drawing Figures

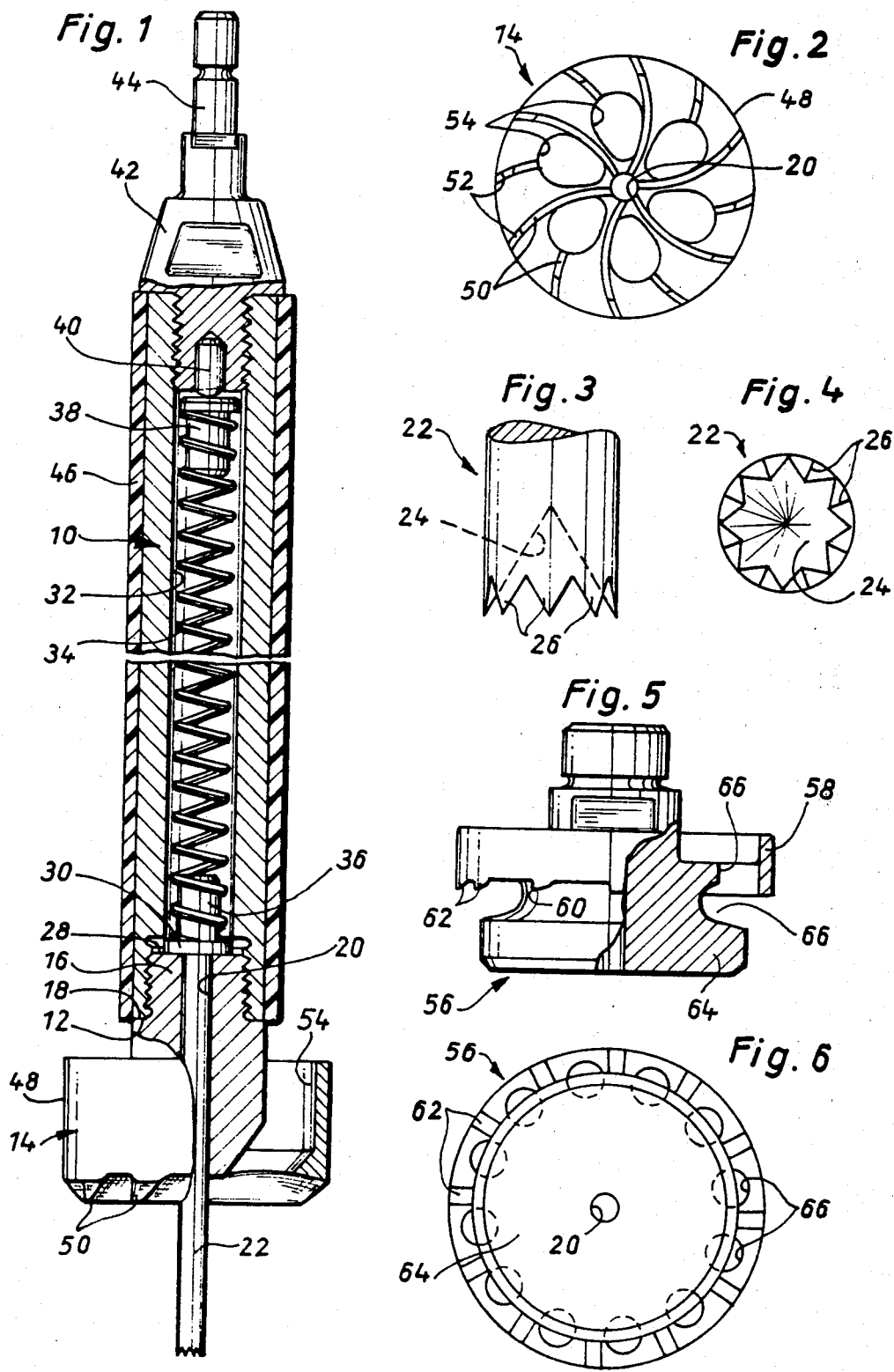

APPARATUS FOR DRILLING BONE

BACKGROUND OF THE INVENTION

The present invention relates to an apparatus for forming holes in bone, especially in hip bone suitable for the insertion of an artificial socket for production of an artificial joint to the femur.

It is necessary that the tool used for this drilling be held carefully in a very precise position since the position of the aperture in the bone is critical for production of a proper artificial joint. Several types of apparatus are already known for maintaining a milling cutter or other drill in the desired working position. For example, optical aids have been used to permit adjustment of the drill. Another possibility is a total endoprosthesis (Judet system) which, similarly to the system described herein, incorporates an elongated tool carrier. This is constructed as a manually retained holding stem by one of whose ends the milling cutter is rotatably retained and can be manually intermittently rotated by means of a tool attached to it.

In several aspects, operation of this type of apparatus calls for technical skill on the part of the surgeon. On the one hand, it is essential that, from the beginning, the milling cutter or other drill is brought into engagement with the femur or other bone in a precise position, and this is a difficult operation since the apparatus must be held with one hand while the milling cutter is rotated with the other hand. Also, unsteadiness of hand resulting from intermittent rotation of the cutter causes canting of the cutter through a relatively small angle which, in turn, can result in bone particles being torn from the femur.

SUMMARY OF THE INVENTION

In more particular terms, it is an object of the present invention to provide an apparatus which can be positioned easily on bone, so that milling of the bone can be performed safely and reliably.

In specific terms, this can be achieved by providing an apparatus suitable for forming a hole in bone, which comprises a body, a drill bit rotatably mounted with respect to the body, and a mandrel coaxial with the drill bit, slidably projectable through the drill bit, and biased to an extended position. Preferably, the mandrel can slide against the bias sufficiently far that it can be made flush with the cutting edge of the drill bit. This biasing is preferably achieved by means of a compression spring within the body. Also, the body preferably comprises an outer casing, and an inner shaft within the outer casing which can rotate within the casing and to which the drill bit is non-rotatably but removably attached. In this case, a compression spring would be housed within the inner shaft.

A supporting and centering mandrel, arranged to slide axially within the body, enables the surgeon to position precisely the apparatus on the bone and to maintain the apparatus in this position during drilling. A driving device can be brought into action to impart continuous rotation to the drill bit, which is preferably a milling cutter. This allows the surgeon to concentrate entirely on guiding the milling cutter, and all he needs to do is to slide axially the body of the apparatus in the direction of the milling cutter.

The apparatus can be correctly positioned without obstruction of the field of view of the surgeon by various adjustment devices which would otherwise be required. This is because the supporting and centering mandrel is positioned at the centre of the milling cutter, and no means need therefore be provided around the cutter for location on the bone.

In one embodiment, the body can be constructed in the manner of a carrier shaft which will rotate in the surgeon's hand when the milling cutter is driven. As a result, it will be possible to provide the end of the shaft distal from the cutter with a connecting member, such as half of a plug coupling, for connection to a motor. As mentioned above, it is preferred that the body comprises an outer casing which will remain stationary when an inner shaft is rotated.

It is convenient to employ a compression spring which can bias the supporting and centering mandrel in its projected position. By providing an adjustment means for the inner shaft the bias provided by the compression spring can be continuously varied so that the force which must be overcome during the cutting operation can be varied to suit individual operations.

The apparatus of the invention is particularly suitable for producing bone apertures for all known artificial joint sockets. The apparatus can be used with particular advantage for producing bone apertures for the kind of total endoprosthesis which has been disclosed by Judet of Paris and which, by contrast with other kinds of prostheses, can be anchored in, for example the femur, without cement.

A milling cutter which forms at least one cylindrically constructed counter-boring tool adapted to cut on its end face is especially suitable for forming bone apertures for this kind of prosthesis.

The axial length of the counter-boring tool is preferably equal to or greater than the depth of the bone aperture to be produced. The advantage of this is that an aperture can be produced in one go, without the need for interrupting the cutter feed in order to remove debris from the aperture. A cutter which is imperforate over its circumference and has a plurality of ducts extending through the cutter and parallel to the axis is preferred since such a cutter will remove debris automatically. Another type of cutter preferred for the same reason is one having cutting teeth extending from the central mandrel to the circumference of the cutter and having a duct provided preferably between each adjacent cutting edge. The cutting edges in this case preferably follow an arcuate path.

As mentioned above, the milling cutter is possibly disposed on the inner shaft so as to be removable, since this has the advantage that different milling cutters can be used successively. It is therefore possible that the edge of a joint socket can be formed uniformly or flat, so that the inserted artificial Judet socket is firmly held not only on the internal circumference of the bone aperture but also on the end face of the aperture. For this reason it can be advantageous to construct the counter-boring tool in a stepped fashion, the circumferential collar of which should be provided with cutting edges on its end face only. Alternatively, the bone aperture can first be produced by means of a cylindrically counter-boring tool which can later be substituted for a face milling cutter having a cylindrical pilot head. This device can be inserted into the bone aperture and the face milling member can be used for facing the edge of the aperture. Advantageous discharge of milling debris can be obtained if the pilot head is undercut and the part of the counter-bore forming the face milling cutter is provided with an axial parallel duct at a radial distance from the circumference.

BRIEF DESCRIPTION OF THE DRAWINGS

The invention is further illustrated by the accompanying drawings, in which:

FIG. 1 shows a longitudinal section of an apparatus for forming a hole in bone;

FIG. 2 is a view of this apparatus from below;

FIG. 3 shows, on a larger scale, a supporting and centering mandrel;

FIG. 4 is an end view of the free end of a mandrel;

FIG. 5 is a partially sectioned side-view of a counter-boring tool for face milling the edge of a bone aperture; and FIG. 6 is a view from below of a counter-boring tool as illustrated in FIG. 5.

DETAILED DESCRIPTION OF THE INVENTION

The apparatus shown in FIG. 1 has a hollow carrier shaft 10 provided, at its lower end as drawn, with an internal screw thread and an annular end face 12 which functions as an abutment for a milling cutter 14 at the front of the shaft. The cutter is formed as a cylindrical counter-boring tool which is screwed into the internal thread by means of an extension sleeve 16. The extension sleeve bears, by means of an annular shoulder 18, on the annular end face 12 so that the cutter is non-rotatably but removably retained by the inner shaft 10. This is to allow the milling cutter to be replaced by one having different characteristics. A central guide bore 20, in which a cylindrical supporting and centering mandrel 22 may be arranged, extends through the extension member 16 and through the milling cutter 14. At its free end, the supporting and centering mandrel can be provided with a mandrel centre for applying the apparatus to the bone to be milled. I prefer, however, that the mandrel is constructed as indicated in FIGS. 3 and 4.

The front end of the mandrel 22 is therefore provided with an internal cone 24 and the annular edge formed on its front end is preferably serrated in a crown configuration with teeth 26. The internal cone 24 ensures that, even when the mandrel rotates, if the mandrel cannot bore substantially into the bone, but nevertheless supports the apparatus steadily while the inner shaft rotates.

When the device is not in use a circumferential collar 30 of the mandrel 22 bears under pressure against the end face 28 of the extension member 16. The contact pressure is produced by compression spring 34 which is disposed in the hollow cylindrical opening 32 of the inner shaft. One end of the spring extends over a retaining stud 36 of the mandrel, while the other end of the spring surrounds a retaining stud 38, which in turn bears centrally on a barrelled end member of an abutment 40 which is provided on the attachment member 42, shown placed at the top end of the inner shaft 10. A coupling member 44, which forms half of a plug coupling, can be plugged into a carrier shaft drive, such as that associated with a motor driving device. An outer casing 46 is supported on the circumference of the carrier shaft 10 so as to be rotatable but prevented from sliding axially.

In use, the surgeon holds the outer casing 46 in which the inner shaft is rotatably supported. To position the apparatus properly, the free end of the mandrel is first applied to the bone, during which time the field of view of the surgeon remains unobstructed all around the milling cutter 14. Displacement of the, as yet stationary, inner shaft relative to the mandrel against the bias of spring 34 enables a test to be made as to whether the selected position on the bone is suitable. Then, rotation of the inner shaft 10 can be begun and the miller cutter 14 set into rotation. By appropriate positioning of his hand, the surgeon must then move inner shaft or the milling cutter into a desired angular position, and then by axial displacement of the inner shaft the bone aperture can be rapidly and precisely cut. During the milling operation the cutter, together with the carrier shaft, moves relative to the mandrel in the axial direction.

The motor drive of the inner shaft and the construction of the cutter ensures that the bone aperture produced has a smooth internal circumference which does not have any irregularities resulting from bone chippings torn from the aperture. To achieve this, the cutter may be provided with an imperforate circumferential surface 48, and accordingly has radial cutting teeth 50 at its bottom end face only. The cutting edge 52 of these teeth is relatively short, from outside to inside as drawn. Between the cutting teeth, parallel axial ducts extend through the cutter automatically to convey milled bone residue upwardly from the bone aperture. For this purpose, the cutting teeth 50 are curved so that the bone residue removed by milling moves automatically between the cutting teeth during rotation of the cutter in the direction of the duct 54. After the bone aperture has been cut, the cutter 14 can be removed from the carrier shaft so that, for example, a face milling cutter 56 as shown in FIGS. 5 and 6 can be used to face the edge of the aperture. This can provide an additional support surface for an artificial ball or socket which is to be inserted into the aperture. The face milling cutter may be provided with a collar 58 which is imperforate over its circumference and has milling teeth 62 having a cutting edge 60 on the underside of the cutter. A cylindrical pilot head 64 may be provided coaxially with the cutting rim to centre the milling cutter in the bone aperture.

Axially parallel ducts 66 may extend through the collar 58 of this milling cutter and may be disposed between the cutting teeth 62 and extend downwardly into a circumferential groove 68 of the pilot head.

I claim:

1. Apparatus suitable for forming a hole in bone, which comprises a body comprising a manually gripable outer casing, an inner shaft rotatably arranged within the casing, a drill bit attached to the lower end of the inner shaft for rotation therewith, and a mandrel coaxial and rotatable with respect to the drill bit, said mandrel being slidably projectable through said drill bit between a retracted and an extended position, means biasing said mandrel to an extended position and teeth on said mandrel for abutting the bone to prevent rotation of the mandrel relative to the bone.

2. Apparatus according to claim 1, in which the mandrel can slide against the bias sufficiently far that it can be made flush with the cutting edge of the drill bit.

3. Apparatus according to claim 1 or claim 2, in which the drill bit is removably attached to the inner shaft.

4. Apparatus according to claim 3, in which the inner shaft lies substantially completely within the outer casing.

5. Apparatus according to claim 3 in which the mandrel is biased to an extended position by a compression spring within the inner shaft.

6. Apparatus according to claim 5, in which the end of the inner shaft distal from the drill bit has means for rotating the inner shaft.

7. Apparatus according to claim 6, in which the means for rotating is half of a plug coupling for connection to a motor.

8. Apparatus according to claim 1 in which the teeth of the mandrel are arranged around its circumference in crowned configuration.

9. The apparatus according to claim 8, in which the teeth define the rim of a substantially conical hole in the end of the mandrel.

10. Apparatus according to claim 1 in which the drill bit is a milling cutter.

11. Apparatus according to claim 10, in which the drill bit is a counter-boring milling cutter.

12. Apparatus according to claim 11, in which the milling cutter has a cutting end face.

13. Apparatus for forming an opening in a bone, more particularly in the hip bone, for the insertion of an artificial joint socket for an artificial hip joint to be provided on the femur, with an elongated tool carrier which is to be manually held in a desired operating position and is equipped on its front end with a milling cutter which is rotatable by a driving device, characterised by a supporting and centering mandrel which projects from the front end face of the milling cutter and is axially slidable in the tool carrier against the action of a force accumulator, is rotatable with respect to the carrier, and has teeth which can abut the bone and prevent rotation of the mandrel with respect to the bone.

14. Apparatus according to claim 13, characterised in that the end of the compression spring which is distal from the mandrel is provided with a contact member, the center of which is in point contact with an abutment in the interior of the carrier shaft.

15. Apparatus according to claim 13, characterised in that the front end of the mandrel is provided with an internal cone and the annular edge formed thereby at the end face of the mandrel is serrated in crowned configuration.

16. Apparatus according to claim 13, in which the milling cutter is a counter-boring tool imperforate over its circumference and having a plurality of ducts extending through the cutter and parallel with its axis.

17. Apparatus according to claim 16, in which cutting teeth of the counter-boring tool have arcuate portions extending from the mandrel to the circumference of the counter-boring tool and one duct is provided between each adjacent cutting edge, more particularly adjacent said arcuate portions.

18. Apparatus according to claim 13, in which the millling cutter is a stepped counter-boring tool, having a serrated cutter, and having cutting edges provided only on the end face of the serrated cutter.

19. Apparatus according to claim 13, in which the milling cutter is a counter-boring tool which forms a face cutter having a cylindrical pilot head.

20. Apparatus according to claim 19, in which the pilot head is undercut and the part of the counter-bore forming the face cutter is provided with an axial parallel duct at a radial distance from the circumference.

* * * * *